United States Patent [19]
Larson et al.

[11] Patent Number: 5,258,534
[45] Date of Patent: Nov. 2, 1993

[54] PREPARATION OF TRIALKYLSILYL NITRILE

[75] Inventors: Gerald L. Larson, Newtown; Thomas V. John, Yardley; Ram R. Chawla, Bensalem, all of Pa.; Chitoor S. Subramaniam, Kendall Park, N.J.

[73] Assignee: Huls America, Inc., Piscataway, N.J.

[21] Appl. No.: 14,231

[22] Filed: Feb. 5, 1993

[51] Int. Cl.$^5$ ............................................. C07F 7/10
[52] U.S. Cl. ................................. 556/415; 252/183.13
[58] Field of Search ..................... 556/415; 252/183.13

[56] References Cited

U.S. PATENT DOCUMENTS

| | | | |
|---|---|---|---|
| 3,032,575 | 5/1962 | Freitag et al. | 556/415 |
| 4,328,351 | 5/1982 | Findeisen et al. | 556/415 |
| 4,429,145 | 1/1984 | Reetz et al. | 556/415 |
| 4,570,009 | 2/1986 | Findeisen et al. | 556/415 |

OTHER PUBLICATIONS

J. V. Seppala, M. Harkonen, "Effect of the Structure of External Alkoxysilane Donors on the Polymerization of Propene with High Activity Ziegler-Natta Catalysts", Makromol. Chem, 190, 2535–2550 (1989).
J. K. Rasmussen, S. M. Heilmann, L. R. Krepski, "The Chemistry of Cyanotrimethylsilane", *Advances in Silicon Chemistry* (Ed. G. L. Larson), vol. 1 (1991).
W. C. Groutas, D. Felker, "Synthetic Application of Cyanotrimethylsilane, Iodotrimethylsilane, Azidotrimethylsilane, and Methylthiotrimethylsilane", *Synthesis*, Nov., 861 (1980).
F. Duboudin, P. Cazeau, F. Moulinas, O. Laporte, "A New One-Pot Synthesis of Silylated Cyanohydrins", *Synthesis*, Mar., 212 (1982).
J. K. Rasmussen, S. M. Heilmann, "A Simple, Safe and Inexpensive Preparation of Trimethylsilyl Cyanide", *Synthesis*, Jul., 523 (1979).
B. Uznanski, "An Improved Preparation of Trimethylsilyl Cyanide", *Synthesis*, Oct., 154 (1978).

*Primary Examiner*—Paul F. Shaver
*Attorney, Agent, or Firm*—Davis Hoxie Faithfull & Hapgood

[57] ABSTRACT

Trialkylsilyl nitrile is prepared by anhydrously reacting stoichiometric amounts of trialkylsilyl halide, hexaalkyldisilazane or trialkylsilyl amine, and hydrogen cyanide, in the absence or presence of a solvent or inert gas atmosphere. No catalyst is necessary, and the reaction preferably is performed at a temperature of from 5° C. to 25° C.

21 Claims, No Drawings

PREPARATION OF TRIALKYLSILYL NITRILE

BACKGROUND OF THE INVENTION

The invention relates to the preparation of trialkylsilyl nitrile (also known as trialkylsilyl cyanide and cyanotrialkylsilane). Trialkylsilyl nitriles, especially trimethylsilyl nitrile, are used to form silylated cyanohydrins from ketones or aldehydes, to conjugatively add cyanide to enones, to form acylnitriles from acyl chlorides, to protect ketones, to add to imines to form a-amino nitriles, and to add to oximes to give a-cyano oximes. Trialkylsilyl nitrile will lead to cycloadducts upon reaction with carbodiimides, diimines, isocyanates and isothiocyanates and nitriles. Further, trialkylsilyl nitrile adds to acetylenes, allenes and nitrones and opens oxiranes and oxetanes. It also serves as a source of cyanide ion in various nucleophilic substitutions, both organic and inorganic. Trimethylsilyl nitrile has been described as one of the most versatile silicon reagents for the purposes of organic synthesis. J.K. Rasmussen, S.M. Heilmann, L.R. Krepski, "The Chemistry of Cyanotrimethylsilane," in *Advances in Silicon Chemistry* (Ed. G.L. Larson), Vol. 1, 66 (1991).

Trialkylsilyl nitrile has been prepared for several years by reaction of the iodosilane $(R)_3SiI$ with silver cyanide according to the reaction

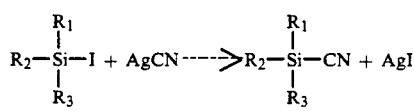

Trimethylsilyl nitrile has also been obtained from the corresponding sulfide, bromide and chloride. W.C. Groutas, D. Felker, "Synthetic Application of Cyanotrimethylsilane, Iodo trimethylsilane, Azidotrimethylsilane, and Methylthio-trimethylsilane," *Synthesis*, Nov., 861 (1980), report obtaining an 80% yield through reaction of silver cyanide with chlorotrimethylsilane. Despite the obvious expense of silver cyanide, it was the reagent of choice for the preparation of trialkylsilyl nitriles for several years. Rasmussen et al. at 68.

Trialkylsilyl nitrile has also been obtained in moderate yields through reaction of chlorotrimethylsilane with potassium mercuricyanide in DMF, reaction of hexamethyldisilazane with hydrogen cyanide, reaction of methoxytriethysilane with pivaloylcyanide in the presence of aluminum chloride, and from cyanide exchange between chlorotriphenysilane and cyanotriethylsilane. Rasmussen et al. at 68-69. The reaction of hexamethyldisilazane with hydrogen cyanide was published by DuPont workers in 1958 in J.Amer.Chem.Soc., 80, 4151-4153 (1958). The DuPont workers disclose a yield of 36.7% trimethylsilyl nitrile and 45% ammonium cyanide. The ammonium cyanide is a nitrile salt and is as such very difficult to handle.

Trimethylsilyl nitrile has been prepared by reacting a diethyl ether solution of trimethylchlorosilane and hydrogen cyanide with a lithium dispersion in petroleum. A modification of this is the subject of U.S. Pat. No. 3,032,575. This has been taken further by first forming lithium cyanide from LiH and hydrogen cyanide, and then preparing trialkylsilyl nitrile from the lithium cyanide.

A moderate yield of 72% trimethylsilyl nitrile has been obtained through reaction of bis(trimethylsilyl)sulfide with dicyanodimethylsilane. M.D. Mizhiritskii, V.O. Reikhsfel'd, *Zh. Obshch. Khim.*, Vol. 55, 1537 (1985). Also, yields of 90-100% have been observed for the synthesis of n-butyldimethylsilyl nitrile, t-butyldimethylsilyl nitrile, and phenyldimethylsilyl nitrile using fluoride ion catalysis. Rasmussen et al. at 71. These reactions involve the following equilibrium:

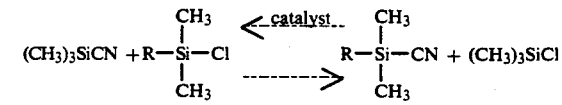

The high yields were generally obtained by distilling the trimethylchlorosilane as it was formed. Rasmussen et al. at 71. It should be noted that for each mole of trialkylsilyl nitrile formed, a mole of trimethylsilyl chloride is formed as a by-product.

Quantitative yields of trimethylsilyl nitrile have been observed from an equimolar mixture of chlorotrimethylsilane and potassium cyanide. F. Duboudin, P. Cazeau, F. Moulines, O. Laporte, "A New, One-Pot Synthesis of Silylated Cyanohydrins," *Synthesis*, Mar., 212 (1982). A 71% yield has also been observed for the same reaction, although the authors noted that scrupulous drying of the glassware and solvent were not performed. J.K. Rasmussen, S.M. Heilmann, "A Simple, Safe and Inexpensive preparation of Trimethylsilyl Cyanide," *Synthesis*, July, 523 (1979). The process, however, generates one mole of potassium chloride as a by-product per mole of trialkylsilyl nitrile. Further, Rasmussen and Heilmann report using anhydrous N-methylpyrrolidone as solvent, which is expensive and difficult to recycle.

The use of hydrogen cyanide is described in B. Uznanski, "An Improved Preparation of Trimethylsilyl Cyanide," *Synthesis*. Oct., 154 (1978). According to Uznanski, trimethylsilyl chloride is reacted with a 25 mol % excess of hydrogen cyanide and triethylamine in diethyl ether giving a 70% yield of trimethylsilyl nitrile. Uznanski's method produces only moderate yields and generates an equimolar amount of triethylamine hydrochloride as a by-product.

The current state of the art involving cyanide salts is described in U.S. Pat. No. 4,429,145, to M.T. Reetz. The Reetz method employs potassium cyanide. The Reetz method uses anhydrous N-methylpyrrolidone as solvent and 10 mol % potassium iodide as a catalyst. Both chemicals are expensive and difficult to recycle.

SUMMARY OF THE INVENTION

Trialkylsilyl nitrile is prepared by anhydrously reacting stoichiometric amounts of trialkylsilyl halide, hexaalkyldisilazane or trialkylsilyl amine, and hydrogen cyanide, in the absence or presence of a solvent or inert gas atmosphere.

DETAILED DESCRIPTION OF THE INVENTION

Under the process of the invention, trialkylsilyl nitrile is prepared through two alternative reactions (I and II) which can be represented by the following equations:

(I) $R_1R_2R_3Si-X + R_1R_2R_3Si-N-H-SiR_1R_2R_3 + 3HCN \rightarrow 3R_1R_2R_3SiCN + NH_4X$ $R_1R_2R_3Si-X + R_1R_2R_3Si-NH_2 + 2HCN \rightarrow 2R_1R_2R_3SiCN + NH_4X$ The reagents, following either equation I or II, are preferably reacted in stoichiometric amounts. Thus, according to equation I, the preferred molar ratios are as follows: trialkylsilyl halide to hydrogen cyanide is 1:3; hexaalkydisilazane to hydrogen cyanide is 1:3; and trialkylsilyl halide to hexaalkyldisilazane is 1:1. According to equation II, the preferred molar ratios are as follows: trialkylsilyl halide to hydrogen cyanide is 1:2; trialkylsilyl halide to trialkylsilyl amine is 1:1; and trialkylsilyl amine to hydrogen cyanide is 1:2. Stoichiometric amounts of reactants are preferred to minimize difficulties related to product purification and safety. A slight excess of the trialkylsilyl halide up to 5% by weight would be tolerable but excess hydrogen cyanide generally should be avoided. The reactants will be substantially within the preferred molar ratios if the preferred molar ratios are adhered to within a margin of plus or minus 0.2.

The substituents ($R_1$, $R_2$, $R_3$) can be as follows, in accord with the invention:

(A) $R_1 = R_2 = R_3 = C_1 - C_6$ alkyl group;

(B) $R_1 = $ t-butyl and $R_2 = R_3 = C_1 - C_6$ alkyl group; and (C) $R_1 = $ aryl group and $R_2 = R_3 = C_1 - C_6$ alkyl group.

For each combination of substituents, (A)-(C), X can be Cl, Br or I. Further, for each arrangement, the $C_1-C_6$ alkyl group can be a branched, unbranched, saturated, unsaturated, substituted or cyclic group, including the isopropyl, isobutyl, sec-butyl, tertbutyl, neopentyl, n-hexyl and the like groups. The aryl group includes the phenyl, benzyl, naphthyl, phenanthryl, anthranyl, and the like groups and generally can include up to three rings. Further, such aryl groups can have one or more substituents including halo, alkyl, aralkyl, aryl, alkoxy, cyano, ether and the like groups.

It should be noted that by using the process of the invention, the formation of the salt as a by-product can be reduced from one mole per mole of trialkylsilyl nitrile to one mole per three moles of trialkylsilyl nitrile. Also, catalysts such as alkali iodides or ion exchange resins are no longer required.

The space yields can be substantially improved by a solvent free process and the product can be obtained in high purity with or without distillation. To limit handling of the toxic product, and to maximize yield and purity, the absence of a solvent is preferred. Where a solvent is employed, solvents such as hexane, octane, toluene, chlorocarbons and the like are preferred. The reaction must be performed under substantially anhydrous conditions, as water decomposes the product. Thus, both the reaction vessel and the reagents should be carefully dried before commencing. The reaction conditions will be substantially anhydrous if the reaction vessel contains less than 1,000 ppm of water.

The reaction, following either equation I or II, should be carried out at a temperature within the suggested range of 0° C. to 60° C., and preferably between 5° C. and 25° C. The reaction can be carried out at a temperature below 0° or exceeding 60° C., but no advantage is apparent in doing so. Further, the suggested range is also useful if different reactants are employed or if the reaction is done under pressure.

An inert gas atmosphere may be applied but is not required. Where an inert gas is employed, the preferred gas is nitrogen due to cost and availability. Other inert gases, such as helium and argon, can also be used. A slight positive pressure of the inert gas is sufficient to maintain an inert atmosphere.

It is advantageous initially to charge the dried reaction vessel with trialkylsilyl halide and either hexaalkyldisilazane (eq. I) or trialkylsilylamine (eq. II) and to stir the mixture. It is also advantageous to feed the hydrogen cyanide into the mixture at a temperature of 5° C. While the hydrogen cyanide is being added, it is preferred to allow the reaction mixture to gradually warm up to 15° C. After addition of the hydrogen cyanide is finished, complete conversion to trialkylsilyl nitrile can be completed at 20° C. in approximately one to thirty six hours.

The trialkylsilyl nitrile obtained by the process can be purified by filtration from the ammonium halide by-product. The ammonium halide can be washed with any hydrocarbon solvent to recover traces of the trialkylsilyl nitrile remaining in the by-product. The yields of trialkylsilyl nitrile obtained according to the invention can exceed 90% of theory. The purity of the trialkylsilyl nitrile obtained is greater than 97%, as determined by gas chromatographic analysis.

To avoid the generation of hydrogen cyanide, the trialkylsilyl nitrile product should not be brought into contact with moisture or hydroxylic solvents. The ammonium halide by-product should be considered to contain small amounts of cyanide and must be handled accordingly.

The following specific examples further illustrate the invention.

EXAMPLE 1

Preparation of Trimethylsilyl Nitrile

One hundred and eighty grams (1.66 moles) of trimethylsilyl chloride and 269 g (1.66 moles) of hexamethyldisilazane were added to a dry reaction vessel under a dry nitrogen atmosphere and stirred. The vessel was then cooled to a temperature of 5° C. and charged with 135 g (5.00 moles) of hydrogen cyanide over a period of 0.5 hour. During the addition of the hydrogen cyanide, the reaction mixture was allowed to warm up to a temperature of 15° C. After addition of the hydrogen cyanide, the reaction mixture was stirred at a temperature of approximately 20° C. for one hour. The trimethylsilyl nitrile was filtered under a nitrogen atmosphere from the white precipitate o ammonium chloride. The ammonium chloride was washed with hexanes (4 × 250 ml) to obtain residual trimethylsilyl nitrile remaining with the by-product. The solvent was removed by distillation, and 448 g of trimethylsilyl nitrile was isolated as a pale yellow residue. The total yield was 98.2% of theory of pure product.

EXAMPLE 2

Preparation of Phenyldimethylsilyl Nitrile 56.8 g (0.33 moles) of phenyldimethylchlorosilane and 95.0 g (0.33 moles) of 1,3 diphenyltetramethyldisilazane were added to a dry reaction vessel under a dry nitrogen atmosphere, stirred and cooled to a temperature of 5° C. 27 g (1.00 moles) of hydrogen cyanide was then added to the reaction mixture over a period of 0.25 hour, during which the reaction mixture was permitted to warm up to a temperature of 20° C. After the hydrogen cyanide was completely added, the reaction mixture was stirred at 20° C. for 24 hours. The ammonium chloride precipitate was removed by filtration and washed with hexanes (2 × 100 ml). The solvent was removed by filtration, and a total amount of 137 g of phenyldimethylsilyl nitrile was obtained as a pale yellow liquid. The yield was 85.1% of theory of product contaminated with small amounts of the starting chlorosilane and the disilazane.

EXAMPLE 3

Preparation of t-Butyldimethylsilyl Nitrile

A dry reaction vessel with an atmosphere of dry nitrogen was charged with 100 ml of pentane as solvent, 37.6 g (0.25 moles) of t-butyldimethylsilyl chloride and 32.7 g (0.25 moles) of t-butyldimethylsilyl amine. The vessel was cooled to a temperature of 5° C. 13.5 g (0.50 moles) of hydrogen cyanide was then added over a period of 0.25 hour, during which the reaction mixture was allowed to warm up to a temperature of 20° C. After addition of the hydrogen cyanide, the reaction mixture was stirred at 20° C. for 12 hours. The ammonium chloride precipitate was filtered from the reaction mixture under a nitrogen atmosphere. The ammonium chloride removed was then washed with pentane (2×100 ml). A total of 61 g of t-butyldimethylsilyl nitrile was obtained, which represented a yield of 86.5% of theory of product contaminated with a small amount of the starting chlorosilane.

EXAMPLE 4

Preparation of t-Butyldiphenylsilyl Nitrile 5.4 g (0.20 moles) of hydrogen cyanide was added over a period of 0.25 hour to a stirred mixture of 25.7 g (0.10 moles) t-butyldiphenylsilyl chloride, 25.5 g (0.10 moles) t-butyldiphenylsilyl amine and 50 ml of toluene as solvent, which was previously charged into a dry vessel and cooled to a temperature of 5° C. During the addition the reaction was allowed to warm up to a temperature of 20° C., while a white solid of ammonium chloride precipitated. After complete addition of the hydrogen cyanide the reaction mixture was stirred at 20° C., filtered under a nitrogen atmosphere and the ammonium chloride cake was washed with toluene (2×50 ml). The combined filtrates were distilled to remove the solvent and 45 g of t-butyldiphenylsilyl nitrile (85% of theory) was isolated as a colorless oil (b.p. 150-151° C./3 mm Hg).

EXAMPLE 5

Preparation of Tri-n-hexylsilyl Nitrile 2.7 g (0.10 moles) of hydrogen cyanide was added over a period of 0.25 hour to a stirred mixture of 16.0 g (0.05 moles) tri-n-hexylsilyl chloride and 15.0 g (0.05 moles) tri-n-hexylsilyl amine, which was previously charged to a dry vessel and cooled to 5° C. During the addition the reaction was allowed to warm up to a temperature of 20° C., while a white solid of ammonium chloride precipitated. After complete addition of the hydrogen cyanide the reaction mixture was stirred at 20° C. for 24 hours. The reaction mixture was then filtered under a nitrogen atmosphere and the ammonium chloride cake was washed with diethyl ether (2×25 ml). The combined filtrates were distilled to remove the solvent and 25 g of tri-n-hexylsilyl nitrile (81% of theory) was isolated as a colorless oil (b.p. 149-151° C./0.2 mm Hg).

What is claimed is:

1. A process for preparing trialkylsilyl nitrile comprising reacting, under substantially anhydrous conditions, trialkylsilyl halide and hexaalkyldisilazane with hydrogen cyanide, wherein the molar ratio of trialkylsilyl halide to hexaalkyldisilazane to hydrogen cyanide is substantially 1:1:3.

2. A process for preparing trialkylsilyl nitrile comprising reacting, under substantially anhydrous conditions, trialkylsilyl halide and trialkylsilyl amine with hydrogen cyanide, wherein the molar ratio of trialkylsilyl halide to trialkylsilyl amine to hydrogen cyanide is substantially 1:1:2.

3. The process of claim 1 wherein the reaction is carried out within the temperature range of from 0° C. to 60° C.

4. The process of claim 2 wherein the reaction is carried out within the temperature range of from 0° C. to 60° C.

5. The process of claim 1 wherein the reaction is carried out within the temperature range of from 5° C. to 25° C.

6. The process of claim 2 wherein the reaction is carried out within the temperature range of from 5° C. to 25° C.

7. The process of claim 1 wherein the reaction is conducted in a solvent.

8. The process of claim 2 wherein the reaction is conducted in a solvent.

9. The process of claim 7 wherein the solvent is pentane.

10. The process of claim 8 wherein the solvent is pentane.

11. The process of claim 1 wherein the reaction is conducted under an inert gas atmosphere.

12. The process of claim 2 wherein the reaction is conducted under an inert gas atmosphere.

13. A process for preparing $(R_1)(R_2)_2Si-CN$ comprising reacting, under substantially anhydrous conditions, $(R_1)(R_2)_2Si-X$ and $(R_1)(R_2)_2Si-NH-Si(R_1)(R_2)_2$ with hydrogen cyanide, wherein X is Cl, Br, or I, and $R_1$ is a t-butyl or aryl group, and $R_2$ is a $C_1-C_6$ alkyl group.

14. A process for preparing $(R_1)(R_2)_2Si-CN$ comprising reacting, under substantially anhydrous conditions, $(R_1)(R_2)_2Si-X$ and $(R_1)(R_2)_2Si-NH_2$ with hydrogen cyanide, wherein X is Cl, Br, or I, and $R_1$ is a t-butyl or aryl group, and $R_2$ is a $C_1-C_6$ alkyl group.

15. A process for preparing $(R)_3Si-CN$ comprising reacting, under substantially anhydrous conditions, $(R)_3Si-X$ and $(R)_3Si-NH-Si(R)_3$ with hydrogen cyanide, wherein X is Cl, Br, or I, and R is a $C_1-C_6$ alkyl group.

16. A process for preparing $(R)_3Si-CN$ comprising reacting, under substantially anhydrous conditions, $(R)_3Si-X$ and $(R)_3Si-NH_2$ with hydrogen cyanide, wherein X is Cl, Br, or I, and R is a $C_1-C_6$ alkyl group.

17. The process of claim 15 wherein R is a methyl group and X is Cl.

18. The process of claim 13 wherein $R_1$ is a phenyl group, $R_2$ is a methyl group, and X is Cl.

19. The process of claim 14 wherein $R_1$ is a t-butyl group, $R_2$ is a methyl group, and X is Cl.

20. A substantially anhydrous reaction mixture for the preparation of $(R_1)(R_2)_2Si-CN$ comprising hydrogen cyanide, $(R_1)(R_2)_2Si-X$ and $(R_1)(R_2)_2Si-NH-Si(R_1)(R_2)_2$ or $(R_1)(R_2)_2Si-NH_2$, wherein X is Cl, Br, or I, and R is a t-butyl or aryl group, and $R_2$ is a $C_1-C_6$ alkyl group.

21. A substantially anhydrous reaction mixture for the preparation of $(R)_3Si-CN$ comprising hydrogen cyanide, $(R)_3Si-X$ and $(R)_3Si-NH-Si(R)_3$ or $(R)_3Si-NH_2$, wherein X is Cl, Br, or I, and R is a $C_1-C_6$ alkyl group.

* * * * *

UNITED STATES PATENT AND TRADEMARK OFFICE
CERTIFICATE OF CORRECTION

PATENT NO. : 5,258,534
DATED : November 2, 1993
INVENTOR(S) : Gerald L. Larson et al.

It is certified that error appears in the above-identified patent and that said Letters Patent is hereby corrected as shown below:

At col. 1, line 12, "a-amino" should read -- $\alpha$-amino --.

At col. 1, line 12, "a-cyano" should read -- $\alpha$-cyano --.

At col. 2, line 67, --(II)-- should appear before "$R_1R_2R_3Si-X$".

At col. 4, line 47, "o" should read --of--.

At col. 6, line 61, claim 20, "R" should read --$R_1$--.

Signed and Sealed this

Twenty-eight Day of February, 1995

Attest:

BRUCE LEHMAN

Attesting Officer

Commissioner of Patents and Trademarks